United States Patent
Chen et al.

(10) Patent No.: US 12,275,692 B2
(45) Date of Patent: Apr. 15, 2025

(54) METHOD FOR PREPARING SODIUM TAURATE AS TAURINE INTERMEDIATE, AND METHOD FOR PREPARING TAURINE

(71) Applicants: ZHEJIANG NHU COMPANY LTD., Zhejiang (CN); ZHEJIANG UNIVERSITY, Zhejiang (CN); SHANGYU NHU BIO-CHEM CO., LTD., Zhejiang (CN); ZHEJIANG NHU PHARMACEUTICAL CO., LTD., Zhejiang (CN)

(72) Inventors: Zhirong Chen, Zhejiang (CN); Xianghua Yao, Zhejiang (CN); Junhua Peng, Zhejiang (CN); Yingxia Pan, Zhejiang (CN); Xiaoxiang He, Zhejiang (CN); Songhua Xu, Zhejiang (CN); Xiaodong Wu, Zhejiang (CN); Xiang Fang, Zhejiang (CN)

(73) Assignees: ZHEJIANG NHU COMPANY LTD., Zhejiang (CN); SHANGYU NHU BIO-CHEM CO., LTD., Zhejiang (CN); ZHEJIANG UNIVERSITY, Zhejiang (CN); ZHEJIANG NHU PHARMACEUTICAL CO., LTD., Zhejiang (CN)

( * ) Notice: Subject to any disclaimer, the term of this patent is extended or adjusted under 35 U.S.C. 154(b) by 923 days.

(21) Appl. No.: 17/424,454

(22) PCT Filed: May 27, 2020

(86) PCT No.: PCT/CN2020/092547
§ 371 (c)(1),
(2) Date: Jul. 20, 2021

(87) PCT Pub. No.: WO2020/238942
PCT Pub. Date: Dec. 3, 2020

(65) Prior Publication Data
US 2022/0081394 A1 Mar. 17, 2022

(30) Foreign Application Priority Data
May 30, 2019 (CN) .......................... 201910463650.2

(51) Int. Cl.
C07C 309/14 (2006.01)
B01D 3/06 (2006.01)
(Continued)

(52) U.S. Cl.
CPC .............. *C07C 309/14* (2013.01); *B01D 3/06* (2013.01); *B01D 61/445* (2013.01); *B01J 3/008* (2013.01);
(Continued)

(58) Field of Classification Search
None
See application file for complete search history.

(56) References Cited

U.S. PATENT DOCUMENTS

| 9,061,976 B1 | 6/2015 | Hu |
| 9,815,778 B1 | 11/2017 | Hu |
| 2016/0355470 A1 | 12/2016 | Hu |

FOREIGN PATENT DOCUMENTS

| CN | 101486669 A | 7/2009 |
| CN | 101508657 A | 9/2009 |

(Continued)

OTHER PUBLICATIONS

WO2020238942 PCT search report (Year: 2021).*
(Continued)

*Primary Examiner* — Sudhakar Katakam
*Assistant Examiner* — Jennifer C Sawyer

(57) ABSTRACT

A method for preparing sodium taurine as a taurine intermediate is provided in the present disclosure. The method comprises the following steps: providing sodium hydroxyethyl sulfonate and an ammonia source; and placing the (Continued)

sodium hydroxyethyl sulfonate and the ammonia source in an aminolysis reactor for an aminolysis reaction to obtain a mixture containing sodium taurine as a taurine intermediate, wherein the molar ratio of ammonia in the ammonia source to the sodium hydroxyethyl sulfonate is greater than or equal to 25:1. A method for preparing taurine is further provided.

8 Claims, 4 Drawing Sheets

(51) Int. Cl.
    *B01D 61/44*     (2006.01)
    *B01J 3/00*     (2006.01)
    *B01J 19/24*     (2006.01)

(52) U.S. Cl.
    CPC ....... *B01J 19/2465* (2013.01); *B01J 19/2475* (2013.01)

(56) References Cited

FOREIGN PATENT DOCUMENTS

| | | | |
|---|---|---|---|
| CN | 104593812 | A | 5/2015 |
| CN | 104628609 | A | 5/2015 |
| CN | 108314634 | A | 7/2018 |
| CN | 210215203 | U | 3/2020 |
| CN | 111269151 | A | 6/2020 |
| DE | 219023 | A3 | 2/1985 |

OTHER PUBLICATIONS

WO2020238942 PCT search report: written opinion (Year: 2021).*
International Search Report & Written Opinion for PCT/CN2020/092547 as prepared by the Chinese International Searching Authority mailed on Jul. 29, 2020, 4 pages.
Liu Fuming, et al., "Research on taurine aminolysis reaction production process", Shandong Chemical Industry, Dec. 16, 2014,. 3 pages.
Wu Yujiang, et al. "Optimization of reaction conditions of taurine aminolysis reaction", Journal of Hubei Polytechnic University, vol. 19, No. 1, Feb. 2004, 4 pages.
Ren Ju et al. "Taurine in the production of crude products of mother liquor of electrodialysis separation process", Anhui Chemical Industry, vol. 42, No. 4, Aug. 2016, 3 pages.

* cited by examiner

METHOD FOR PREPARING SODIUM TAURATE AS TAURINE INTERMEDIATE, AND METHOD FOR PREPARING TAURINE

CROSS-REFERENCE TO RELATED APPLICATIONS

This application claims priority to and is a 35 U.S.C. § 371 national phase application of PCT/CN2020/092547 (WO2020/238942), filed on May 27, 2020, entitled "Method For Preparing Sodium Taurate as Taurine Intermediate, and Method For Preparing Taurine", which application claims priority to and the benefit of Chinese Patent Application No. 201910463650.2, filed May 30, 2019, the disclosures of which are incorporated herein by reference in their entirety.

TECHNICAL FIELD

The present disclosure relates to the field of preparing taurine, in particular, to an aminolysis reaction system, a method for preparing sodium taurine as a taurine intermediate and a method for preparing the taurine.

BACKGROUND

Taurine (i.e., 2-aminoethane-sulfonic acid)), which is also called as taurocholic acid or ethylamine sulfonic acid, is a white crystal or powder, odourless, non-poisonous, and acescency. Taurine is a non-protein amino acid, which is one of the important amino acids and necessary for human body. It has unique pharmacological and nutritional health effects. Taurine can be widely used in fields such as a medicine, food additives, a fluorescent whitening agent, organic synthesis and the like. It can also be used as a biochemical reagent, a wetting agent, a buffer and the like. Taurine have been widely used as medicine and food additives in western developed countries.

SUMMARY

In one aspect, the present disclosure provides a method for preparing sodium taurine as taurine intermediate, including following steps:

providing sodium hydroxyethyl sulfonate and an ammonia source;

feeding the sodium hydroxyethyl sulfonate and the ammonia source into an aminolysis reactor to carry out the aminolysis reaction, so as to obtain a mixture containing sodium taurine as a taurine intermediate, wherein a molar ratio of ammonia in the ammonia source to the sodium hydroxyethyl sulfonate is greater than or equal to 25:1.

In some embodiments, the molar ratio of the ammonia in the ammonia source to the sodium hydroxyethyl sulfonate is in a range of 25:1 to 100:1; and in other embodiments, in a range of 30:1 to 50:1.

In some embodiments, the method further includes:

after the aminolysis reaction, separating unreacted ammonia from the mixture with an ammonia separating device, so as to obtain an ammonia-containing gas and the taurine intermediate, respectively, wherein the ammonia separating device is connected to the aminolysis reactor;

compressing the ammonia-containing gas with a compression unit to obtain a supercritical fluid containing ammonia, and circulating the supercritical fluid to the aminolysis reactor, wherein the compression unit is connected to the ammonia separating device and the aminolysis reactor, respectively.

In some embodiments, the ammonia separating device includes one ammonia separator.

In some embodiments, the ammonia separating device includes two ammonia separators, which are defined as a first ammonia separator and a second ammonia separator, respectively.

The first ammonia separator is connected to the aminolysis reactor. The first ammonia separator is configured for separating unreacted ammonia from the mixture after the aminolysis reaction to obtain a first ammonia-containing gas and a first residuum mixture.

The second ammonia separator is connected to the first ammonia separator. The second ammonia separator is configured for further separating the ammonia gas from the first residuum mixture to obtain a second ammonia-containing gas and a second residuum, and circulating the second ammonia-containing gas to the first ammonia separator.

In some embodiments, the compression unit includes a first compression unit and a second compression unit.

The first compression unit is connected to the first ammonia separator and the aminolysis reactor, respectively. The first compression unit is configured for compressing the ammonia-containing gas in the first ammonia separator to obtain the supercritical fluid, and circulating the supercritical fluid to the aminolysis reactor.

The second compression unit is connected to the first ammonia separator and the second ammonia separator, respectively. The second compression unit is configured for circulating the second ammonia-containing gas to the first ammonia separator.

In some embodiments, the ammonia separating device includes a plurality of sequentially arranged ammonia separators. A number of the plurality of ammonia separators is n, and n is an integer which is greater than 2 and less than 20.

A first ammonia separator of the plurality of ammonia separators is connected to the aminolysis reactor, the first ammonia separator is configured for separating the unreacted ammonia from the mixture after the aminolysis reaction to obtain a first ammonia-containing gas and a first residuum mixture.

A second ammonia separator of the plurality of ammonia separators is connected to the first ammonia separator, the second ammonia separator is configured for further separating ammonia gas from the first residuum mixture to obtain a second ammonia-containing gas and a second residuum, and circulating the second ammonia-containing gas to the first ammonia separator.

An $i^{th}$ ammonia separator of the plurality of ammonia separators is connected to an $i\text{-}1^{th}$ ammonia separator, wherein i is an integer which is greater than 2 and less than or equal to n, the $i^{th}$ ammonia separator is configured for further separating ammonia gas from an $i\text{-}1^{th}$ residuum mixture to obtain an $i^{th}$ ammonia-containing gas and an $i^{th}$ residuum, and circulating the $i^{th}$ ammonia-containing gas to the $i\text{-}1^{th}$ ammonia separator.

In some embodiments, the aminolysis reaction system further includes a plurality of compression units, a number of the plurality of compression units is n.

A first compression unit of the plurality of compression units is connected to the $1^{st}$ ammonia separator and the aminolysis reactor, respectively, and the first compression unit is configured for compressing the ammonia-containing gas in the first ammonia separator to obtain the supercritical fluid, and circulating the supercritical fluid to the aminolysis reactor.

A second compression unit of the plurality of compression units is connected to the first ammonia separator and the second ammonia separator, respectively, and the second compression unit is configured for circulating the second ammonia-containing gas to the first ammonia separator.

An $i^{th}$ compression unit of the plurality of compression units is connected to the i-1$^{th}$ ammonia separator and the $i^{th}$ ammonia separator, respectively, and the $i^{th}$ compression unit is configured for circulating the $i^{th}$ ammonia-containing gas to the i-1$^{th}$ ammonia separator.

In some embodiments, the aminolysis reaction system includes a plurality of sequentially arranged ammonia separators and a plurality of compression units. The number of the plurality of ammonia separator is n and the number of compression units is n, and n is three or four.

In some embodiments, the ammonia source is at least one of ammonium hydroxide mixture and liquid ammonia.

In some embodiments, the method further includes a step of supplementing the ammonia source into the ammonia separating device.

In another aspect, the present disclosure provides a method for preparing taurine, which includes following steps:

providing sodium hydroxyethyl sulfonate and the ammonia source;

feeding the sodium hydroxyethyl sulfonate and the ammonia source into an aminolysis reactor for an aminolysis reaction to obtain a mixture containing sodium taurine as a taurine intermediate, wherein a molar ratio of ammonia in the ammonia source to the sodium hydroxyethyl sulfonate is greater than or equal to 25:1; and acidizing the taurine intermediate to obtain the taurine.

In some embodiments, the molar ratio of the ammonia in the ammonia source to the sodium hydroxyethyl sulfonate is in a range of 25:1 to 100:1; and in other embodiments, the molar ratio of the ammonia in the ammonia source to the sodium hydroxyethyl sulfonate is in a range of 30:1 to 50:1.

In some embodiments, the method further includes following steps:

after the aminolysis reaction and before acidizing the taurine intermediate, separating unreacted ammonia from the mixture with an ammonia separating device, so as to obtain an ammonia-containing gas and the sodium taurine as the taurine intermediate, respectively; and compressing the ammonia-containing gas with a compression unit to obtain a supercritical fluid containing ammonia, and circulating the supercritical fluid to the aminolysis reactor.

In some embodiments, acidizing the taurine intermediate with a bipolar membrane to obtain the taurine and sodium hydroxide.

In some embodiments, the sodium hydroxyethyl sulfonate is made from ethylene oxide and sodium hydrogen sulfite. The sodium hydrogen sulfite is made from sulfur dioxide and at least a part of the sodium hydroxide which is obtained by acidizing the taurine intermediate with the bipolar membrane.

The method for preparing the sodium taurine as the taurine intermediate and the method for preparing taurine have following advantages. By improving the percentage of the ammonia source in reactants of the aminolysis reaction, the aminolysis reaction can be sufficiently carried out, so that the yield of the reaction can be largely increased.

Furthermore, unreacted ammonia can be separated from the reaction system by an ammonia separating device to obtain an ammonia-containing gas. The ammonia-containing gas can be compressed with a compression unit to obtain a supercritical fluid. The supercritical fluid can be circulated to an aminolysis reactor. In this process, of ammonia can be completely recycled with relatively small energy consumption. That is, the unreacted ammonia is recycled and subjected to the aminolysis reaction again, so as to improve the ammonia content in the aminolysis reaction and largely decrease the production cost. Moreover, after transforming the ammonia-containing gas into the supercritical fluid, the supercritical fluid can have relatively high temperature and pressure. Therefore, when the supercritical fluid is circulated to the aminolysis reactor, the energy of the supercritical fluid will be conducive to the ammonolysis process in the aminolysis reactor and form a high-temperature and high-pressure condition, so as to lower the energy consumption.

BRIEF DESCRIPTION OF THE DRAWINGS

In order to better describe and explain the embodiments and/or examples of those inventions disclosed herein, one or more drawings may be referred to. The additional details or examples used to describe the drawings should not be considered as limiting the scope of any of the disclosed inventions, the currently described embodiments and/or examples, and the best mode of these inventions currently understood.

Figure 1:
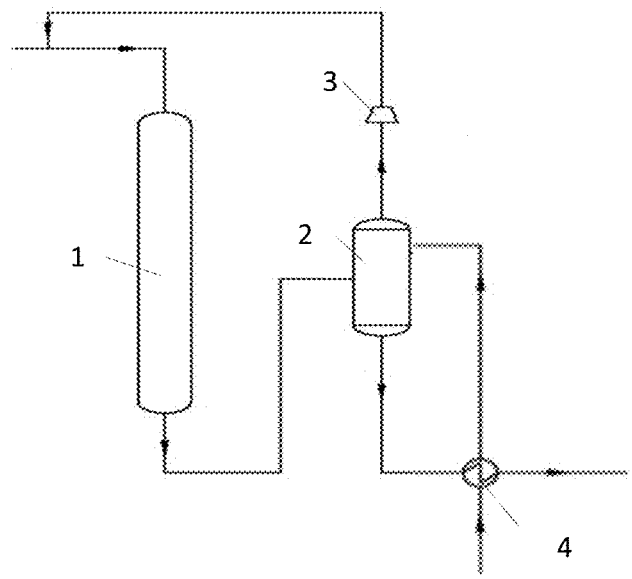
FIG. 1 is a structural schematic diagram of an ammonia separating device being used for preparing sodium taurine as a taurine intermediate in one embodiment of the present disclosure.

The methods for preparing taurine mainly include biological extraction, fermentation method and chemical synthesis methods. Among them, chemical synthesis methods are researched and developed the fastest. According to different raw materials and processes, there are currently more than 20 chemical synthesis methods for preparing the taurine. However, due to restrictions on the source of raw materials, production costs, product yield, synthesis process conditions, equipment requirements and the like, there are only two methods that are used in industrial production.

(1) Ethanolamine method: ethanolamine method for preparing the taurine includes two steps by using ethanolamine. In detail, the ethanolamine method can be divided into esterification process, chlorination process, and ethylenimine process. Among them, the raw materials of the esterification method are easy to obtain, and the yield of the esterification method is higher than other methods. Therefore, it is adopted by most manufacturers at home and abroad. The raw materials of the esterification method are ethanolamine, sulfuric acid, and sodium sulfite. Firstly, sulfuric acid and ethanolamine are esterified to synthesize an intermediate 2-aminoethyl sulfate. Then, the intermediate is sulfonated with sodium sulfite or ammonium sulfite to synthesize taurine. The reaction equations are shown hereinafter:

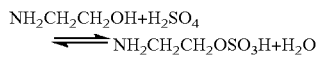

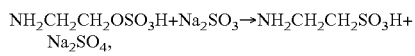

or

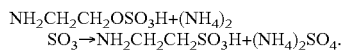

Since the esterification is a reversible reaction, the reaction is not complete, which limits a conversion rate and yield of the ethanolamine. Moreover, sodium sulfate can be prepared in the reaction system, and it is difficult to separate sodium sulfate from the reaction system. This will influence yield and quality of the product, and this method is not environmentally friendly.

(2) Ethylene oxide method: ethylene oxide is used as the raw material in the ethylene oxide method. The ethylene oxide is firstly subjected to ring-opening addition with sodium sulfite, and then reacts with the ammonia to synthesize sodium taurine under conditions of heating and pressure. The sodium taurine is further acidized to obtain the taurine. The reaction process can be shown hereinafter.

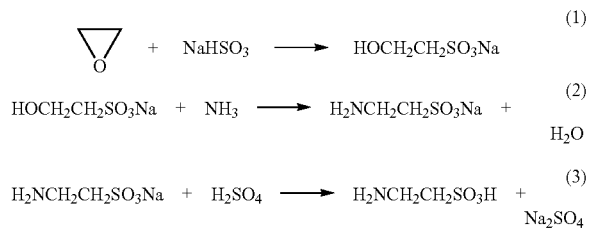

The side reaction can be shown hereinafter.

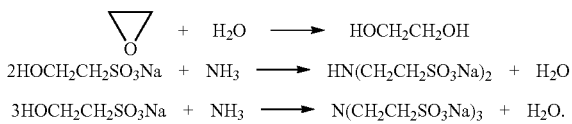

The ethylene oxide method includes steps of addition, aminolysis and acidizing. A yield of the ethylene oxide is higher than that of the ethanolamine method, and the ethylene oxide method is widely used at present.

The ammonolysis step and the acidizing step in the ethylene oxide method are key steps for preparing the taurine. U.S. Pat. No. 1,932,907 discloses aminolysis reaction of isethionate and amines, wherein a molar ratio of the ammonia to the isethionate was 6.8:1. After reacting at temperature in a range of 240 degrees centigrade to 250 degrees centigrade for 2 hours, a yield of sodium taurine was only 80%. German patent No. DD219023A3 discloses composition of aminolysis product of sodium hydroxyethyl sulfonate. When a molar ratio of the ammonia to the sodium hydroxyethyl sulfonate was in a range of 10:1 to 20:1 and alkali metal or alkali metal hydroxides were added into the reaction system as a catalyst, an aminolysis product containing 71% of sodium taurine and 29% of sodium ditaurine and sodium tritaurine were obtained after reacting at temperature between 200 degrees centigrade and 290 degrees centigrade for 5 minutes to 45 minutes. The maximum yield of the reaction was only 64%. In view of this, when preparing sodium taurine by aminolysis method from sodium hydroxyethyl sulfonate, it was apt to obtain by products such as ditaurate and tritaurate. The aminolysis reaction between the sodium hydroxyethyl sulfonate and the ammonia was a reversible reaction, which has un-obvious heat effect. In the process of this patent, since a molar ratio of the ammonia to the sodium hydroxyethyl sulfonate was low and the ammonia was soluble in a liquid phase, although an excessive amount of ammonia was used, the amount of ammonia in the liquid phase during the reaction was much lower than the designed molar ratio of the ammonia to the sodium hydroxyethyl sulfonate. This caused a large number of side reactions, and obtained by-products such as ditaurate and tritaurate, thereby causing low yield of the sodium taurine. In order to increase yield of aminolysis reaction, some researches have been done. For example, in Chinese patent No. CN105732440 and Chinese patent No. CN108314633, aminolysis reaction liquid was neutralized with acid to obtain mother liquor, and all or most of the mother liquor was circulated to an aminolysis reactor. The more the mother liquor was added, the higher the yield of the aminolysis reaction was. In the above patents, the mother liquor was circulated and successively subjected to aminolysis reaction, so that the yield increased greatly. However, the mother liquor not only contained the by-product ditaurate and tritaurate, but also contained a plurality of impurities such as sodium sulfate, ethylene glycol, polyethylene glycol, trace metal elements and the like. When the untreated mother liquor was circulated into the system continuously, the impurities in the system would accumulate along with the increasing of cycle numbers, and was adverse to the reaction. If the untreated mother liquor was discharged directly, pollutant of the mother liquor was in a high concentration, which is harmful to the environment. Moreover, when the mother liquor was circulated and subjected to aminolysis reaction, it needed to supplement ammonia to the aminolysis reactor. In order to meet a high-temperature and high-pressure condition for aminolysis reaction, and the mother liquor and the supplemented ammonia needed to be heated and pressurized again. The required heat would be increased by a large margin, and was adverse to industrial production.

In the process for preparing taurine, ammonia is added in excessive amount in the aminolysis reaction. After the aminolysis reaction, deamination treatment should be carried out. Generally, the aminolysis liquid has relatively high temperature and pressure, and an ammonia-containing gas generated in the deamination treatment generally has certain heat. Some researchers are focus on how to recycle and use this part of heat. For example, in Chinese patent No. CN101528658, a method for treating aminolysis liquid was disclosed. The aminolysis liquid was subjected to first flashing, second flashing falling film evaporating and multiple-effect falling film evaporating, respectively. The steam of flashing was used as a heat source of the next evaporator. However, this patent was silent to the treatment of the recycled ammonia. Conventional methods for reusing the ammonia of a deamination resultant are shown hereinafter. For a resultant having ammonia in a high content, the resultant is condensed and circulated to the aminolysis reactor. For a resultant having ammonia in a low content, the resultant is firstly refined with equipment such as ammonia still and the like, circulated and reused when the ammonia content reaches a certain concentration. However, when the treated ammonia is circulated to the aminolysis reactor, it should be pressurized and heated to meet the high-temperature high-pressure condition for aminolysis reaction. This will consume much energy. The conventional art does not disclose a method for circulating the ammonia with low energy consumption.

In addition, some researchers use agents such as sulfuric acid, hydrochloric acid and the like in the acidizing process of sodium taurine. For example, in patents U.S. Pat. No. 9,061,976, CN101486669 and CN101508657, sulfuric acid or sulphurous acid were used to carry out the acidification. A large number of inorganic salts such as sodium sulfate will be obtained in the acidizing process with the sulfuric acid. The inorganic salts will cause problems, such as being difficultly removed from the reaction system, blockage of equipment, high cost of production and the like.

DETAILED DESCRIPTION

The technical solutions in the embodiments of the present disclosure will be described clearly and completely hereinafter. Obviously, the described embodiments are only a part of the embodiments of the present disclosure, rather than all of the embodiments. Based on the embodiments of the present disclosure, all other embodiments obtained by those of ordinary skill in the art without creative work shall fall within the protection scope of the present disclosure.

The present disclosure provides a method for preparing sodium taurine as taurine intermediate, which includes following steps:

S1, providing sodium hydroxyethyl sulfonate and an ammonia source.

S2, feeding the sodium hydroxyethyl sulfonate and the ammonia source into an aminolysis reactor for an aminolysis reaction to obtain a mixture containing sodium taurine as a taurine intermediate, wherein a molar ratio of ammonia in the ammonia source to the sodium hydroxyethyl sulfonate is greater than or equal to 25:1.

In step S1, the ammonia in the ammonia source can be the aminating agent. The ammonia source can be at least one of ammonium hydroxide mixture and ammonia liquid. The mass fraction of the ammonia in the ammonium hydroxide mixture can be in a range of 20% to 30%. Since a higher percentage of the ammonia in the aminolysis system can promote the aminolysis reaction to proceed towards direction of forward reaction and reach higher yield of the sodium taurine as taurine intermediate, the molar ratio of the ammonia in the ammonia source to the sodium hydroxyethyl sulfonate can be defined as greater than 25:1. In some embodiments, the molar ratio of the ammonia in the ammonia source to the sodium hydroxyethyl sulfonate can be in a range of 25:1 to 100:1. For example, when the molar ratio of the ammonia in the ammonia source to the sodium hydroxyethyl sulfonate is 25:1, the yield of the sodium taurine as the taurine intermediate can be greater than or equal to 85%. When the molar ratio of the ammonia in the ammonia source to the sodium hydroxyethyl sulfonate is s 100:1, the yield of the sodium taurine as the taurine intermediate can be greater than 95%.

In step S2, the aminolysis reactor can be the container of the aminolysis reaction. Temperature of the aminolysis reaction can be in a range of 250 degrees centigrade to 290 degrees centigrade. Pressure of the aminolysis reaction can be in a range of 10 MPa to 20 MPa. Duration of the aminolysis reaction can be in a range of 0.5 hours to 3.0 hours.

Furthermore, in order to obtain the higher percentage of the ammonia in the ammonia source as defined in step S1, raw materials containing high amount of the ammonia can be provided. Alternatively, in step S3, unreacted ammonia in the aminolysis reaction can be recycled and used as the raw material of the aminolysis reaction.

S3, separating unreacted ammonia from the mixture with an ammonia separating device, so as to obtain an ammonia-containing gas and the sodium taurine as the taurine intermediate, respectively.

Therein, the ammonia-containing gas can be directly conveyed into the aminolysis reactor; alternatively, can be subjected to following step S4.

S4, compressing the ammonia-containing gas with a compression unit to obtain a supercritical fluid containing ammonia, and circulating the supercritical fluid to the aminolysis reactor.

The ammonia separating device and the compression unit will be further described in details hereinafter.

The ammonia separating device can include one ammonia separator, tow ammonia separators or a plurality of ammonia separators, which will be described hereinafter, respectively.

Referring to FIG. 1, in one embodiment, the ammonia separating device can be a single ammonia separator, that is, includes only one ammonia separator 2. The ammonia separator 2 can be connected to the aminolysis reactor 1. The ammonia separator 2 can be configured for separating the unreacted ammonia from residuum after the aminolysis reaction to obtain the ammonia-containing gas. The compression unit 3 can be connected to the aminolysis reactor 1 and the ammonia separator 2, respectively. That is, the compression unit 3 can be located between the aminolysis reactor 1 and the ammonia separator 2. The compression unit 3 can be configured for compressing the ammonia-containing gas to obtain the supercritical fluid, and circulating the supercritical fluid to the aminolysis reactor 1.

The aminolysis reactor 1 can be a high-temperature and high-pressure reactor, and can be a reaction zone for preparing the sodium taurine as the taurine intermediate. In some embodiments, the aminolysis reactor can be a high-pressure autoclave, a tubular reactor or a synthesis tower; and in other embodiments, the aminolysis reactor 1 can be the tubular reactor.

The ammonia separator 2 can be a device that separates the ammonia from the reaction system by methods of evaporation or flashing. In some embodiments, when the ammonia separator 2 is a flash evaporator with some pressure, it can obtain better ammonia separation effect. When the ammonia-containing gas is discharged from the ammonia separator 2, the ammonia-containing gas can have certain heat and pressure. In other words, a part of energy in the mixture obtained by the aminolysis reaction can be transferred into the ammonia-containing gas having certain temperature and pressure, so as to make full use of the waste heat.

The compression unit 3 can be a compressor, which is configured for compressing the ammonia-containing gas to obtain the supercritical fluid containing ammonia. In this process, the ammonia-containing gas can be conveyed to the compression unit 3 through the ammonia separator 2. The volume of the ammonia-containing gas can be reduced and the internal energy of the ammonia-containing gas can be increased, thereby obtaining the supercritical fluid. It should be noted that, the supercritical fluid can at least include supercritical ammonia. The supercritical fluid can include gaseous water and possible supercritical water. Compared with the ammonia-containing gas, the supercritical fluid has relatively high temperature and relatively high pressure. In this process, it can be interpreted as follows: a part of work by the compressor is used to overcome the potential energy between gas molecules in the ammonia-containing gas, resulting in the ammonia-containing gas transforming into the supercritical fluid having smaller intermolecular distance; and the other part of work by the compressor turns into kinetic energy of gas molecules, resulting in the supercritical fluid having relatively high temperature and relatively high pressure.

When the supercritical fluid is circulated to the aminolysis reactor 1, the supercritical fluid can be directly mixed with the sodium hydroxyethyl sulfonate raw material to obtain the mixture. Then, the mixture can be conveyed to the aminolysis reactor to react. The supercritical fluid can not only heat the raw materials and facilitate preheating the raw materials, but also increase the temperature and pressure in the aminolysis reactor 1, so as to provide high-pressure and high-temperature reaction conditions for aminolysis reaction, thereby saving energy. In addition, the ammonia in the supercritical fluid can be the raw material for the reaction, and increase the concentration of ammonia in the aminolysis reaction. This can facilitate proceeding of the reaction, improving yield of the product and reducing yield of by-products, thereby reducing the cost.

Figure 2:
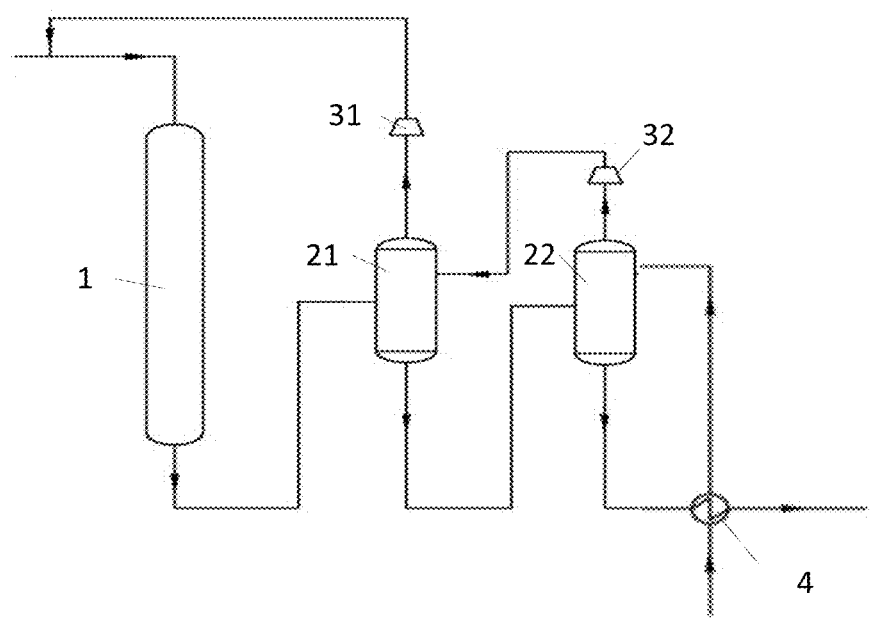
FIG. 2 is a structural schematic diagram of an ammonia separating device being used for preparing sodium taurine as a taurine intermediate in another embodiment of the present disclosure.

Referring to FIG. 2, in another embodiment, the ammonia separating device can be a two-stage ammonia separator, i.e., including two ammonia separators: a first ammonia separator 21 and a second ammonia separator 22. The first ammonia separator 21 can be connected to the aminolysis reactor 1. The second ammonia separator 22 can be connected to the first ammonia separator 21. The first ammonia separator 21 can be configured for separating unreacted ammonia gas from the mixture after the aminolysis reaction to obtain a first ammonia-containing gas and a first residuum mixture. The second ammonia separator 22 can be configured for further separating the ammonia gas from the first residuum mixture to obtain a second ammonia-containing gas and a second residuum, and circulating the second ammonia-containing gas to the first ammonia separator 21. The first ammonia-containing gas and the second ammonia-containing gas can be mixed, and conveyed to the first compression unit 31. That is, the ammonia-containing gas in the first ammonia separator 21 can be a summation of the first ammonia-containing gas and the second ammonia-containing gas. By this step-by-step reflux method, the pressure can be gradually increased, making load of the first compression unit 31 not unduly large while compressing, so that the ammonia-containing gas can be easily compressed into the supercritical fluid.

The first compression unit 31 can be connected to the first ammonia separator 1 and the aminolysis reactor 21, respectively. That is, the first compression unit 31 can be located between the aminolysis reactor 1 and the first ammonia separator 21. The first compression unit 31 can be the same as the compression unit 3. The first compression unit 31 can be configured for compressing the ammonia-containing gas in the first ammonia separator 21 to obtain the supercritical fluid, and circulating the supercritical fluid to the aminolysis reactor 1.

In this embodiment, the second ammonia separator 22 can be configured for further separating the ammonia gas from the first residuum mixture. This process can be configured for further improving the recycle of ammonia, and can take full advantage of waste heat. It could be understood that, in order to make the second ammonia-containing gas successfully enter the first ammonia separator 21, a gas pump or a second compression unit 32 can be provided. In some embodiments, the second compression unit 32 can be disposed. An operating temperature and an operating pressure of the second compression unit 32 can be adjusted, so that the second ammonia-containing gas can have certain temperature and pressure, thereby facilitating the second ammonia-containing gas being transformed into the supercritical fluid with the first compression unit 31 after entering the first ammonia separator 21.

Figure 3:
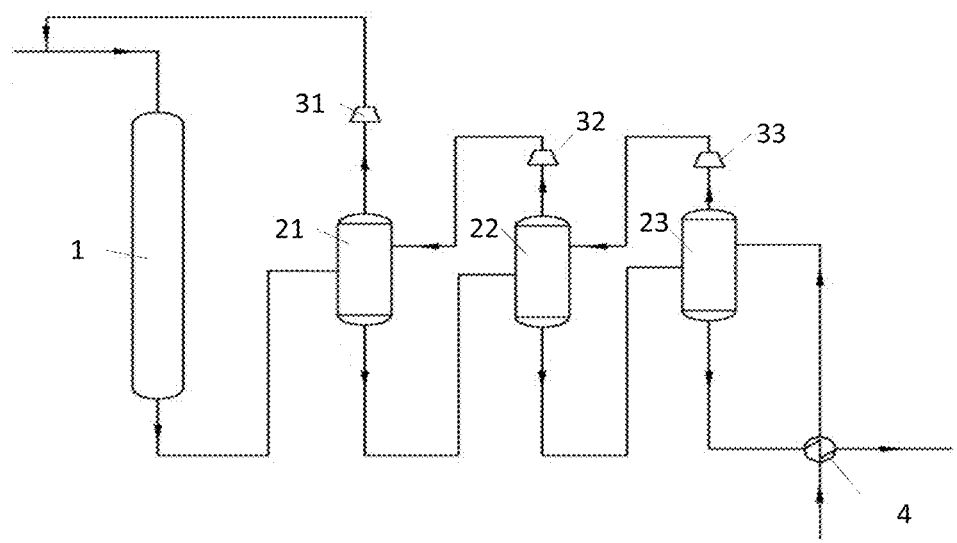
FIG. 3 is a structural schematic diagram of an ammonia separating device being used for preparing sodium taurine as a taurine intermediate in another embodiment of the present disclosure.

Referring to FIG. 3, in another embodiment, the ammonia separating device can be a three-stage ammonia separator, i.e., including a first ammonia separator 21, a second ammonia separator 22 and a third ammonia separator 23. Therein, the first ammonia separator 21 can be connected to the aminolysis reactor 1. The second ammonia separator 22 can be connected to the first ammonia separator 21. The third ammonia separator 23 can be connected to the second ammonia separator 22. The first ammonia separator 21 can be configured for separating unreacted ammonia gas from the mixture after the aminolysis reaction to obtain a first ammonia-containing gas and a first residuum mixture. The second ammonia separator 22 can be configured for further separating the ammonia gas from the first residuum mixture to obtain a second ammonia-containing gas and a second residuum, and circulating the second ammonia-containing gas to the first ammonia separator 21. The third ammonia separator 23 can be configured for further separating the ammonia gas from the second residuum mixture to obtain a third ammonia-containing gas and a third residuum, and circulating the third ammonia-containing gas to the second ammonia separator 22 and further circulating to the first ammonia separator 21. At this moment, the ammonia-containing gas in the first ammonia separator 21 can include the first ammonia-containing gas, the second ammonia-containing gas and the third ammonia-containing gas, that is, the ammonia-containing gas in the first ammonia separator 21 can be a summation of the ammonia-containing gases in each ammonia separator.

The first compression unit 31 can be connected to the first ammonia separator 1 and the aminolysis reactor 21, respectively. That is, the first compression unit 31 can be located between the aminolysis reactor 1 and the first ammonia separator 21. The first compression unit 31 can be the same as the compression unit 3. The first compression unit 31 can be configured for compressing the ammonia-containing gas in the first ammonia separator 21 to obtain the supercritical fluid, and circulating the supercritical fluid to the aminolysis reactor 1.

In this embodiment, the second ammonia separator 22 can be configured for further separating the ammonia gas from the first residuum mixture, and the third ammonia separator 23 can be configured for further separating the ammonia gas from the second residuum mixture. This process can be configured for further improving the recycle of ammonia, and can take full advantage of waste heat. It could be understood that, in order to make the second ammonia-containing gas successfully enter the first ammonia separator 21, and make the third ammonia-containing gas successfully enter the second ammonia separator 22, a gas pump or a compression unit (such as a second compression unit 32, a third compression unit 33) can be provided. An operating temperature and an operating pressure of the second compression unit 32 and the third compression unit 33 can be adjusted, so that the second ammonia-containing gas and the third ammonia-containing gas can have certain temperature and pressure, thereby facilitating the third ammonia-containing gas and the second ammonia-containing gas being transformed into the supercritical fluid with the first compression unit 31 after the third ammonia-containing gas successively entering the second ammonia separator 22 and the first ammonia separator 21, and the second ammonia-containing gas entering the first ammonia separator 21.

Therefore, the ammonia separating device can be not limited to a two-stage ammonia separator and a three-stage ammonia separator, and can be a multi-stage ammonia separator. In other words, the multi-stage ammonia separator can separate the ammonia gas step by step. The separated ammonia gas can be directly circulated to the aminolysis reactor with the compression unit to react; alternatively, can be refluxed step by step, and finally can be compressed to the supercritical fluid with the first compression unit 31. At this moment, the energy of the reacted mixture can be recycled and aggregated step by step. The ammonia separating device can be shown hereinafter.

In another embodiment, the ammonia separating device can include a plurality of sequentially arranged ammonia separators, a number of the plurality of ammonia separators is n, and n is an integer which is greater than 2 and less than 20.

A $1^{st}$ ammonia separator of the plurality of ammonia separators is connected to the aminolysis reactor. The $1^{st}$ ammonia separator is configured for separating the unreacted ammonia from the mixture after the aminolysis reaction to obtain a $1^{st}$ ammonia-containing gas and a $1^{st}$ residuum mixture A $2^{nd}$ ammonia separator of the plurality of ammonia separators is connected to the $1^{st}$ ammonia separator. The $2^{nd}$ ammonia separator is configured for further separating ammonia gas from the $1^{st}$ residuum mixture to obtain a $2^{nd}$ ammonia-containing gas and a $2^{nd}$ residuum, and circulating the $2^{nd}$ ammonia-containing gas to the $1^{st}$ ammonia separator An $i^{th}$ ammonia separator of the plurality of ammonia separators is connected to an $i\text{-}1^{th}$ ammonia separator, wherein i is an integer which is greater than 2 and less than or equal to n, the $i^{th}$ ammonia separator is configured for further separating ammonia gas from an $i\text{-}1^{th}$ residuum mixture to obtain an $i^{th}$ ammonia-containing gas and an $i^{th}$ residuum, and circulating the $i^{th}$ ammonia-containing gas to the $i\text{-}1^{th}$ ammonia separator The aminolysis reaction system further comprises a plurality of compression units, a number of the plurality of compression units is n. A $1^{st}$ compression unit of the plurality of compression units is connected to the $1^{st}$ ammonia separator and the aminolysis reactor, respectively. The $1^{st}$ compression unit is configured for compressing the ammonia-containing gas in the $1^{st}$ ammonia separator to obtain the supercritical fluid, and circulating the supercritical fluid to the aminolysis reactor;

A $2^{nd}$ compression unit of the plurality of compression units is connected to the $1^{st}$ ammonia separator and the $2^{nd}$ ammonia separator, respectively, and the $2^{nd}$ compression unit is configured for circulating the $2^{nd}$ ammonia-containing gas to the $1^{st}$ ammonia separator.

An $i^{th}$ compression unit of the plurality of compression units is connected to the $i\text{-}1^{th}$ ammonia separator and the $i^{th}$ ammonia separator, respectively, and the $i^{th}$ compression unit is configured for circulating the $i^{th}$ ammonia-containing gas to the $i\text{-}1^{th}$ ammonia separator.

In some embodiments, the aminolysis reaction system includes a plurality of sequentially arranged ammonia separators and a plurality of compression units. The number of the plurality of ammonia separator is n and the number of compression units is n, and n is three or four.

Furthermore, the present method can further include a step of supplementing the ammonia source into the ammonia separating device. By supplementing the ammonia source by the ammonia separating device, the supplemented ammonia source can be refluxed to the compression unit via single-stage ammonia separator or multi-stage ammonia separators step by step, and can be compressed into the supercritical fluid with the recycled ammonia. In some embodiments, before conveying the supplemented ammonia source into the ammonia separating device, the supplemented ammonia source can firstly exchange heat with the ammonia-removed taurine intermediate (sodium taurine) mixture with a heat exchanger 4, so as to increase the temperature of the supplemented ammonia source, and then can be conveyed to the ammonia separating device.

Figure 4:
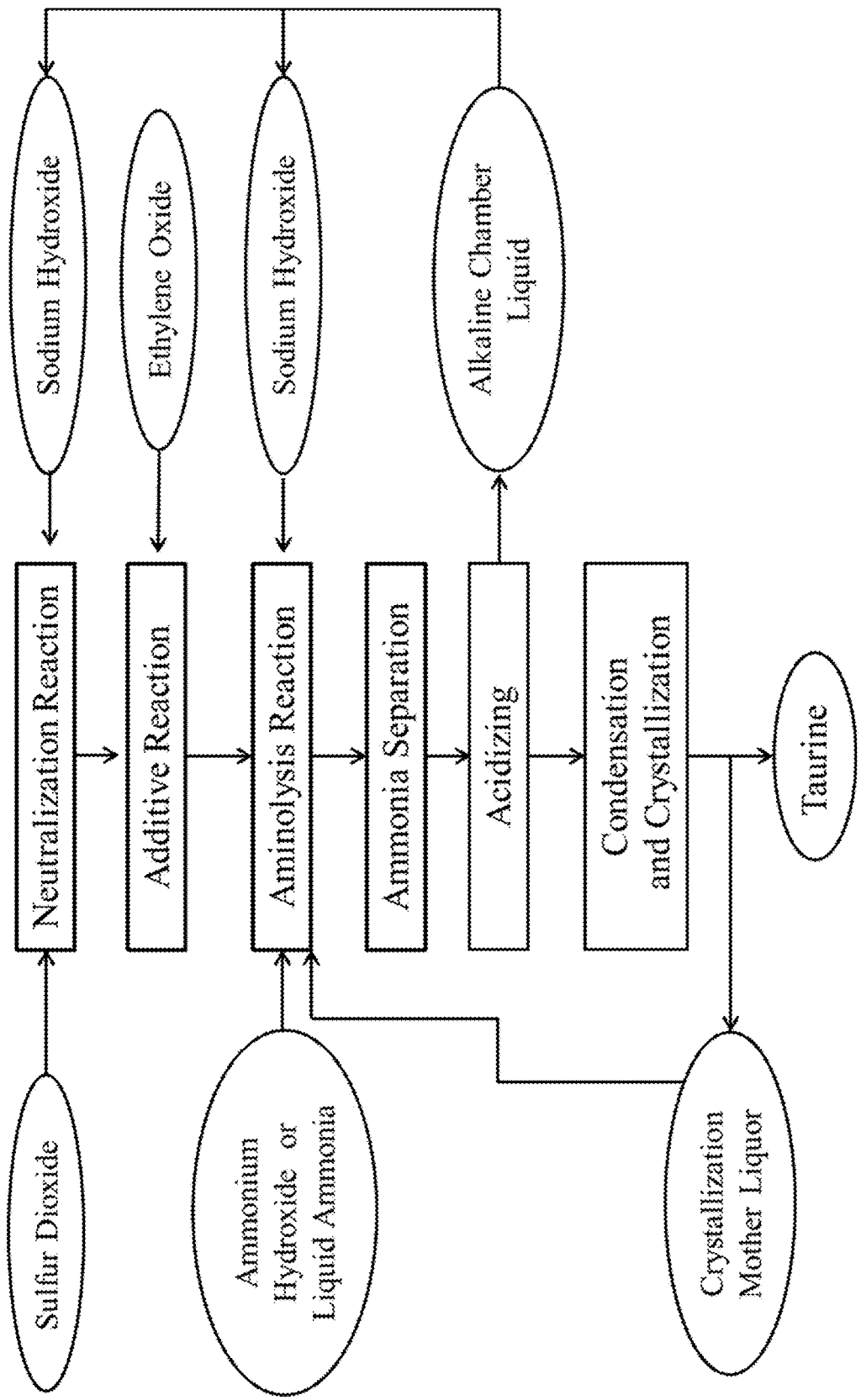
FIG. 4 is a flow chart of a method for preparing taurine in the present disclosure.

Referring to FIG. 4, the present disclosure further provides a method for preparing taurine, which can include following methods:

S10, providing sodium hydroxyethyl sulfonate and the ammonia source;

S20, feeding the sodium hydroxyethyl sulfonate and the ammonia source into the aminolysis reactor to carry out the aminolysis reaction, so as to obtain the mixture containing the sodium taurine as the taurine intermediate, wherein the molar ratio of the ammonia in the ammonia source to the sodium hydroxyethyl sulfonate is greater than 25:1; and S30, acidizing the sodium taurine as taurine intermediate to obtain the taurine;

Between step S20 and step S30, the method can further include following steps.

S201, separating the unreacted ammonia from the mixture with the ammonia separating device, so as to obtain the ammonia-containing gas and the sodium taurine as the taurine intermediate, respectively;

S202, compressing the ammonia-containing gas with the compression unit to obtain the ammonia-containing supercritical fluid, and circulating the supercritical fluid to the aminolysis reactor.

Therein, the step S201 and the step S202 can refer to the step S3 and step S4, respectively, and are not described in details hereinafter. After the mixture obtained in step S20 is treated by the ammonia separating device, a mass fraction of the sodium taurine can be in a range of 2% to 30%; and in some embodiment, can be in a range of 10% to 25%.

In step S30, the taurine intermediate (sodium taurine) can be acidized by a bipolar membrane to obtain the taurine and sodium hydroxide.

Figure 5:
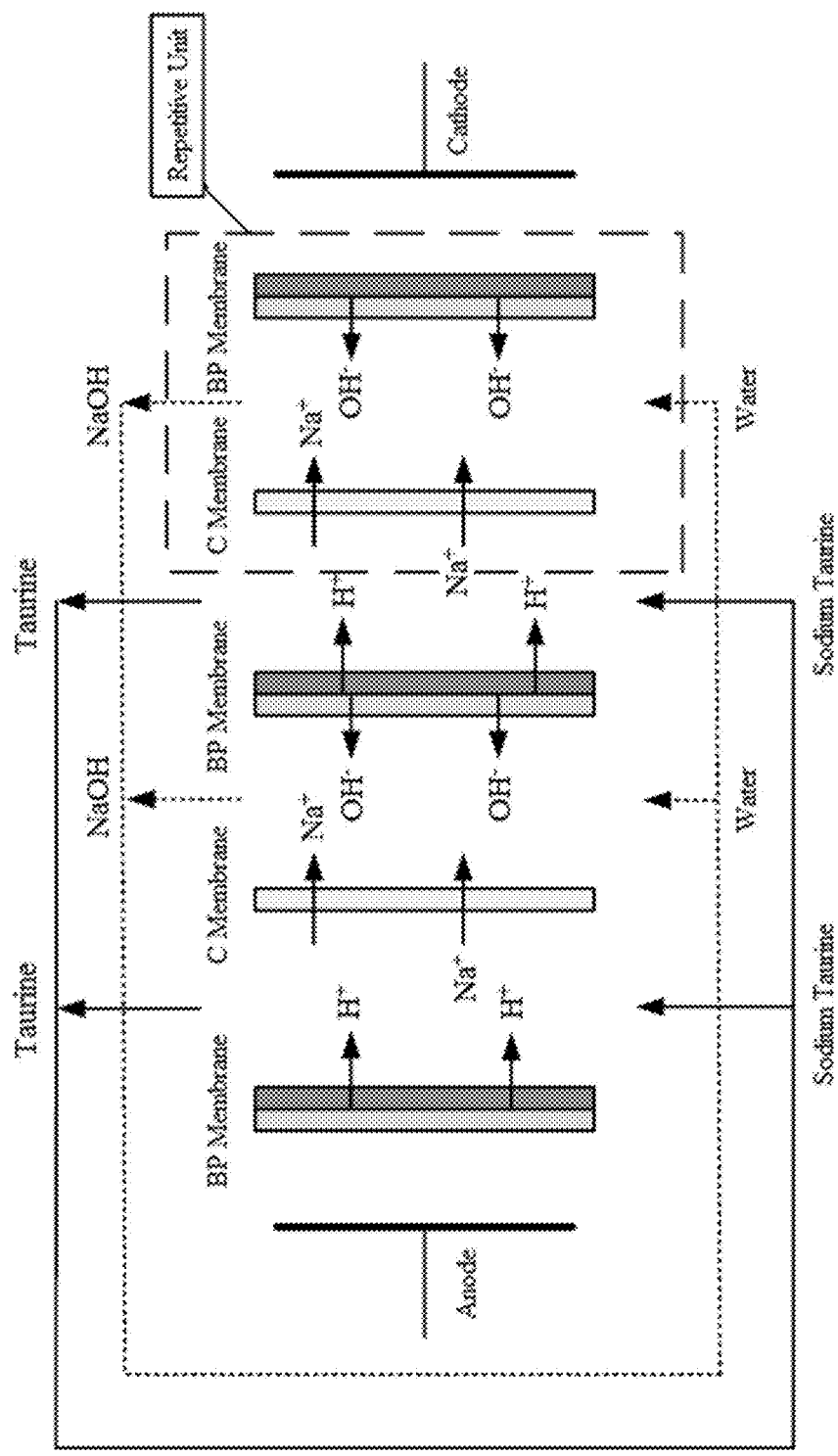
FIG. 5 is a schematic diagram of an acidizing process in the method for preparing taurine in the present disclosure.

Referring to FIG. 5, a three-chambered bipolar membrane electrodialysis device can be used to carry out the acidization. The device can have an anode and a cathode, and a bipolar membrane (i.e., BP membrane) and a cation exchange membrane (i.e., C membrane) can be alternately disposed between the anode and the cathode. The taurine intermediate (sodium taurine) solution obtained in step S30 can be conveyed to a feed liquid chamber of the bipolar membrane electrodialysis device. Water can be conveyed to an alkali chamber which is not in contact with the feed liquid chamber. Sodium hydroxide aqueous solution can be conveyed to a cathode chamber and an anode chamber as conducting medium. Under the effect of electric field, sodium ions of the sodium taurine solution in the feed liquid chamber can permeate through the cation exchange membrane and enter the alkali chamber to combine with the hydroxyl ion generated by ionizing water to form sodium hydroxide. The resultant can be discharged from the alkali chamber. Hydrogen ions generated by ionizing water can permeate through the bipolar membrane and combine with the taurate ions in the feed liquid chamber to form the taurine. The taurine can be discharged from the feed liquid chamber.

The discharged taurine can be further concentrated and crystallized to obtain a taurine product. After the taurine is crystalized, the obtained crystallization mother liquor can be circulated to the step S20 and subjected to aminolysis reaction again. In consideration of catalytic action of alkali on aminolysis reaction, the sodium hydroxide obtained in step S30 can be circulated to the step S20 and subjected to the aminolysis reaction along with the crystallization mother liquor after taurine crystallization.

It should be understand that before step S10, the sodium hydroxyethyl sulfonate can be prepared from ethylene oxide and sodium hydrogen sulfite. The sodium hydrogen sulfite can be prepared from sodium hydroxide and sulfur dioxide. Therefore, the sodium hydroxide obtained in the step S30 can be used to prepare the sodium hydroxyethyl sulfonate, so as to reuse the resultants. The processes in some embodiments can be shown hereinafter:

(1) Adding sulfur dioxide into an alkali liquid to obtain a sodium hydrogen sulfite solution; and (2) Providing ethylene oxide, and subjecting the ethylene oxide and the obtained sodium hydrogen sulfite solution to addition reaction to obtain a sodium hydroxyethyl sulfonate-containing solution.

Wherein the alkali liquid in step (1) can be a sodium hydroxide solution. A mass fraction of sodium hydroxide in the sodium hydroxide solution can be in a range of 3% to 30%. In some embodiments, the mass fraction of sodium hydroxide in the sodium hydroxide solution can be in a range of 5% to 20%. A pH value of the sodium hydrogen sulfite solution can be in a range of 3.5 to 7.0. In some embodiments, the pH value of the sodium hydrogen sulfite solution can be in a range of 4.0 to 6.5.

In step (2), a pH value of the sodium hydrogen sulfonate-containing solution can be greater than 10.0. In some embodiments, the pH value of the sodium hydrogen sulfonate solution-containing can be greater than 11.0. A mass fraction of the sodium hydroxyethyl sulfonate in the sodium hydroxyethyl sulfonate solution can be in a range of 10% to 20%.

In the present disclosure, bipolar membrane acidizing method is used to prepare the taurine. Compared with conventional sulfuric acid or hydrochloric acid acidizing technology, acid consumption can be reduced and production of by-products sodium sulfate or sodium chloride can be avoided. Moreover, the obtained sodium hydroxide can be circulated, which largely decrease raw material cost and solid waste treatment cost. Since no inorganic salt is prepared, the separating and purifying technology is much simpler, and equipment cost and production cost can be decreased. The whole production can circulated without waste gas, waste water and waste residue, and can be industrialized.

In the present disclosure, the method for preparing the taurine intermediate and the method for preparing taurine have following advantages.

By improving the percentage of the ammonia source in reactants of the aminolysis reaction, the aminolysis reaction can be sufficiently carried out, so that the yield of the reaction can be largely increased.

Furthermore, unreacted ammonia can be separated from the reaction system by an ammonia separating device to obtain an ammonia-containing gas. The ammonia-containing gas can be compressed with a compression unit to obtain a supercritical fluid. The supercritical fluid can be circulated to an aminolysis reactor. In this process, complete cycle of ammonia can be carried out with relatively small energy consumption. That is, the unreacted ammonia is recycled and subjected to the aminolysis reaction again, so as to improve the ammonia content in the aminolysis reaction and largely decrease the production cost. Moreover, after transforming the ammonia-containing gas into the supercritical fluid, the supercritical fluid has relatively high temperature and pressure. Therefore, when the supercritical fluid is circulated to the aminolysis reactor, the energy of the supercritical fluid can be conveyed to the aminolysis reactor and form a high-temperature high-pressure condition needed in the aminolysis process, so as to lower the energy consumption.

The method for preparing the taurine intermediate and the method for preparing the taurine in the present disclosure will be further described in conjunction with embodiments hereinafter.

Embodiment 1

200 Kg ammonium hydroxide (which had a concentration of 25% by mass) and 101 Kg liquid ammonia were added into 170 Kg sodium hydroxyethyl sulfonate aqueous solution (which had a concentration of about 15% by mass) to obtain a mixture, wherein a molar ratio of the ammonia to the sodium hydroxyethyl sulfonate was 25:1. The mixture was pressurized to 18 MPa, then preheated to 280 degrees centigrade with a pre-heater, and conveyed to an aminolysis reactor to react. Temperature of the aminolysis reaction was 280 degrees centigrade, and the pressure of the aminolysis reaction was 18 MPa. After reacting for 30 minutes, the ammonia was removed from the aminolysis liquid to obtain 320 Kg sodium taurine solution, wherein the content of sodium taurine was 7.2% by mass and the yield of the sodium taurine was 90.9%.

Embodiment 2

200 Kg ammonium hydroxide (which had a concentration of 25% by mass) and 372 Kg liquid ammonia were added into 170 Kg sodium hydroxyethyl sulfonate aqueous solution (which had a concentration of about 15% by mass) to obtain a mixture, wherein a molar ratio of the ammonia to the sodium hydroxyethyl sulfonate was 70:1. The mixture was pressurized to 18 MPa, then preheated to 280 degrees centigrade with a pre-heater, and conveyed to an aminolysis reactor to react. Temperature of the aminolysis reaction was 280 degrees centigrade, and the pressure of the aminolysis reaction was 17.8 MPa. After reacting for 30 minutes, the ammonia was removed from the aminolysis liquid to obtain 319 Kg sodium taurine solution, wherein the content of sodium taurine was 7.82% by mass and the yield of the sodium taurine was 98.4%.

Embodiment 3

An aminolysis reaction system as shown in FIG. 1 was used in embodiment 3.

A mixture of the ammonium hydroxide and the liquid ammonia was added into a sodium hydroxyethyl sulfonate aqueous solution, mixed and pressurized with a high-pressure pump. The resultant mixture was preheated, reacted in an aminolysis reactor, and treated with an evaporator to obtain a gaseous phase mixture. The gaseous phase mixture was pressurized, recycled and directly mixed with the sodium hydroxyethyl sulfonate aqueous solution. The resultant was conveyed to the aminolysis reactor to react. The supplemented ammonia gas was subjected to heat exchange with evaporated liquor and conveyed to the aminolysis reactor via the evaporator. After the reaction reached equilibrium, the molar ratio of the ammonia to the sodium hydroxyethyl sulfonate was controlled to be at 30:1 in the reaction system.

The technological conditions of embodiment 3 were shown hereinafter. A sodium hydroxyethyl sulfonate aqueous solution (which had a concentration of 15% by mass) was pressurized to 18 MPa via a high-pressure pump, and directly mixed with the pressurized recycled ammonia to obtain a resultant mixture. A flow rate of the sodium hydroxyethyl sulfonate aqueous solution was 272 Kg per hour. The resultant mixture was heated to 280 degrees centigrade. The resultant mixture was conveyed to the aminolysis reactor and reacted in conditions at 18 MPa and 280 degrees centigrade. The reaction lasted for 30 minutes, and an aminolysis liquid was obtained. The aminolysis liquid was conveyed to the evaporator, the operating pressure of the evaporator was 0.1 MPa, and the operating temperature of the evaporator was 88.9 degrees centigrade. A first ammonia-containing gas discharged from the evaporator was compressed to 300 degrees centigrade and 18.2 MPa, and circulated to the aminolysis reactor. The first liquid discharged from the evaporator can be subjected to heat exchange with the supplemented ammonia to obtain a sodium taurine solution. The flow rate of the sodium taurine was 279 Kg per hour, and the supplemented ammonia was added at a flow rate of 8.0 Kg per hour.

Contents of each component in the in the sodium taurine solution was tested. The content of sodium taurine was 13.7%, the content of sodium ditaurine was 1.1%, and the content of sodium tritaurine was 0.09%. The yield of the sodium taurine can be calculated, and was 94.3%.

In embodiment 3, unit consumption of the sodium taurine was 2.16 tons standard coal for 1 ton sodium taurine.

Embodiment 4

An aminolysis reaction system as shown in FIG. 2 was used in embodiment 4.

A mixture of the ammonium hydroxide and the liquid ammonia was added into a sodium hydroxyethyl sulfonate aqueous solution, mixed and pressurized with a high-pressure pump. The resultant mixture was preheated, reacted in an aminolysis reactor, and sequentially treated with a first flash tank and a second evaporator, respectively. The gaseous phase mixture obtained in the second evaporator was pressurized, recycled and conveyed to the first flash tank. The gaseous phase mixture obtained in the first flash tank was pressurized, recycled and directly mixed and heated with the sodium hydroxyethyl sulfonate aqueous solution. The resultant was conveyed to the aminolysis reactor to react. The supplemented ammonia gas was conveyed to the aminolysis reactor via the second evaporator. After the reaction reached equilibrium, the molar ratio of the ammonia to the sodium hydroxyethyl sulfonate was controlled to be at 30:1 in the reaction system.

The technological conditions of embodiment 4 were shown hereinafter. A sodium hydroxyethyl sulfonate aqueous solution (which had a concentration of 15% by mass) was pressurized to 18 MPa via a high-pressure pump, and directly mixed with the pressurized recycled ammonia to obtain a resultant mixture. A flow rate of the sodium hydroxyethyl sulfonate aqueous solution was 272 Kg per hour. The resultant mixture was heated to 280 degrees centigrade. The resultant mixture was conveyed to the aminolysis reactor and reacted in conditions at 18 MPa and 280 degrees centigrade. The reaction lasted for 30 minutes, and an aminolysis liquid was obtained. The aminolysis liquid was conveyed to the first flash tank and subjected to flashing, the operating pressure of the first flashing was 8 MPa and the operating temperature of the first flashing was 220 degrees centigrade. A first ammonia-containing gas discharged from the first flash tank was compressed to a state of 300 degrees centigrade and 18.2 MPa, and circulated to the aminolysis reactor. The first liquid discharged from the first flash tank was conveyed to the second evaporator. The operating pressure of the second evaporator was 0.1 MPa, and the operating temperature of the second evaporator was 87.8 degrees centigrade. A second ammonia-containing gas discharged from the second evaporator was compressed to 210 degrees centigrade and 8.2 MPa, and circulated to the first flash tank to flash. The second liquid discharged from the second evaporator can be subjected to heat exchange with the supplemented ammonia to obtain a sodium taurine solution. The flow rate of the sodium taurine was 279 Kg per hour, and the supplemented ammonia was added at a flow rate of 8.0 Kg per hour.

Contents of each component in the in the sodium taurine solution was tested. The content of sodium taurine was 13.8%, the content of sodium ditaurine was 1.09%, and the content of sodium tritaurine was 0.08%. The yield of the sodium taurine can be calculated, and was 94.9%.

In embodiment 4, unit consumption of the sodium taurine was 1.07 tons standard coal for 1 ton sodium taurine.

Embodiment 5

An aminolysis reaction system as shown in FIG. 3 was used in embodiment 5.

A mixture of the ammonium hydroxide and the liquid ammonia was added into a sodium hydroxyethyl sulfonate aqueous solution, mixed and pressurized with a high-pressure pump. The resultant mixture was preheated, reacted in an aminolysis reactor, and sequentially treated with a first flash tank, a second flash tank and a third evaporator, respectively. The gaseous phase mixture obtained in the third evaporator was pressurized, recycled and conveyed to the second flash tank. The gaseous phase mixture obtained in the second flash tank was pressurized, recycled and conveyed to the first flash tank. The gaseous phase mixture obtained in the first flash tank was pressurized, recycled and directly mixed and heated with the sodium hydroxyethyl sulfonate aqueous solution. The resultant was conveyed to the aminolysis reactor to react. The supplemented ammonia gas was conveyed to the aminolysis reactor via the third evaporator. After the reaction reached equilibrium, the molar ratio of the ammonia to the sodium hydroxyethyl sulfonate was controlled to be at 30:1 in the reaction system.

The technological conditions of embodiment 5 were shown hereinafter. A sodium hydroxyethyl sulfonate aqueous solution (which had a concentration of 15% by mass) was pressurized to 18 MPa via a high-pressure pump, and directly mixed with the pressurized recycled ammonia to obtain a resultant mixture. A flow rate of the sodium hydroxyethyl sulfonate aqueous solution was 272 Kg per hour. The resultant mixture was heated to 280 degrees centigrade. The resultant mixture was conveyed to the aminolysis reactor and reacted in conditions at 18 MPa and 280 degrees centigrade. The reaction lasted for 30 minutes, and an aminolysis liquid was obtained. The aminolysis liquid was conveyed to the first flash tank and subjected to flashing, the operating pressure of the first flashing was 8 MPa and the operating temperature of the first flashing was 245.5 degrees centigrade. A first ammonia-containing gas discharged from the first flash tank was compressed to a state of 300 degrees centigrade and 18.2 MPa, and circulated to the aminolysis reactor. The first liquid discharged from the first flash tank was conveyed to the second flash tank. The operating pressure of the second flash tank was 3 MPa, and the operating temperature of the second evaporator was 203.4 degrees centigrade. A second ammonia-containing gas discharged from the second evaporator was compressed to 290 degrees centigrade and 8.2 MPa, and circulated to the first flash tank to flash. A second liquid discharged from the second flash tank was conveyed to the third evaporator. The operating pressure of the evaporator was 0.1 MPa, and the operating temperature of the evaporator was 97 degrees centigrade. A third ammonia-containing gas discharged from the third evaporator was compressed to 210 degrees centigrade and 3.1 MPa, and circulated to the second flash tank to flash. The third liquid discharged from the third evaporator can be subjected to heat exchange with the supplemented ammonia to obtain a sodium taurine solution. The flow rate of the sodium taurine was 279 Kg per hour, and the supplemented ammonia was added at a flow rate of 8.0 Kg per hour.

Contents of each component in the in the sodium taurine solution was tested. The content of sodium taurine was 13.9%, the content of sodium ditaurine was 1%, and the content of sodium tritaurine was 0.08%. The yield of the sodium taurine can be calculated, and was 95.68%.

In embodiment 5, unit consumption of the sodium taurine was 0.65 tons standard coal for 1 ton sodium taurine.

Embodiment 6

The same operating method in embodiment 5 was used in embodiment 6, and the molar ratio of the ammonia to the sodium hydroxyethyl sulfonate in the control system was 40:1.

The technological conditions of embodiment 6 were shown hereinafter. A sodium hydroxyethyl sulfonate aqueous solution (which had a concentration of 15% by mass) was pressurized to 18 MPa via a high-pressure pump, and directly mixed with the pressurized recycled ammonia to obtain a resultant mixture. A flow rate of the sodium hydroxyethyl sulfonate aqueous solution was 272 Kg per hour. The resultant mixture was heated to 280 degrees centigrade. The resultant mixture was conveyed to the aminolysis reactor and reacted in conditions at 18 MPa and 280 degrees centigrade. The reaction lasted for 30 minutes, and an aminolysis liquid was obtained. The aminolysis liquid was conveyed to the first flash tank and subjected to flashing, the operating pressure of the first flashing was 8 MPa and the operating temperature of the first flashing was 243 degrees centigrade. A first ammonia-containing gas discharged from the first flash tank was compressed to a state of 300 degrees centigrade and 18.2 MPa, and circulated to the aminolysis reactor. A first liquid discharged from the first flash tank was conveyed to the second flash tank. The operating pressure of the second flash tank was 3 MPa, and the operating temperature of the second evaporator was 203 degrees centigrade. A second ammonia-containing gas discharged from the second evaporator was compressed to 290 degrees centigrade and 8.2 MPa, and circulated to the first flash tank to flash. A second liquid discharged from the second flash tank was conveyed to the third evaporator. The operating pressure of the evaporator was 0.1 MPa, and the operating temperature of the evaporator was 97 degrees centigrade. A third ammonia-containing gas discharged from the third evaporator was compressed to 210 degrees centigrade and 3.1 MPa, and circulated to the second flash tank to flash. The third liquid discharged from the third evaporator can be subjected to heat exchange with the supplemented ammonia to obtain a sodium taurine solution. The flow rate of the sodium taurine was 279 Kg per hour, and the supplemented ammonia was added at a flow rate of 8.0 Kg per hour.

Contents of each component in the in the sodium taurine solution was tested. The content of sodium taurine was 14.1%, the content of sodium ditaurine was 0.71%, and the content of sodium tritaurine was 0.05%. The yield of the sodium taurine can be calculated, and was 97.1%.

In embodiment 6, unit consumption of the sodium taurine was 0.74 tons standard coal for 1 ton sodium taurine.

Embodiment 7

The same operating method in embodiment 5 was used in embodiment 7, and the molar ratio of the ammonia to the sodium hydroxyethyl sulfonate in the control system was 50:1.

The technological conditions of embodiment 7 were shown hereinafter. A sodium hydroxyethyl sulfonate aqueous solution (which had a concentration of 15% by mass) was pressurized to 18 MPa via a high-pressure pump, and directly mixed with the pressurized recycled ammonia to obtain a resultant mixture. A flow rate of the sodium hydroxyethyl sulfonate aqueous solution was 272 Kg per hour. The resultant mixture was heated to 280 degrees centigrade. The resultant mixture was conveyed to the aminolysis reactor and reacted in conditions at 18 MPa and 280 degrees centigrade. The reaction lasted for 30 minutes, and an aminolysis liquid was obtained. The aminolysis liquid was conveyed to the first flash tank and subjected to flashing, the operating pressure of the first flashing was 8 MPa and the operating temperature of the first flashing was 241 degrees centigrade. A first ammonia-containing gas discharged from the first flash tank was compressed to a state of 300 degrees centigrade and 18.2 MPa, and circulated to the aminolysis reactor. A first liquid discharged from the first flash tank was conveyed to the second flash tank. The operating pressure of the second flash tank was 3 MPa, and the operating temperature of the second evaporator was 203 degrees centigrade. A second ammonia-containing gas discharged from the second evaporator was compressed to 290 degrees centigrade and 8.2 MPa, and circulated to the first flash tank to flash. A second liquid discharged from the second flash tank was conveyed to the third evaporator. The operating pressure of the evaporator was 0.1 MPa, and the operating temperature of the evaporator was 97 degrees centigrade. A third ammonia-containing gas discharged from the third evaporator was compressed to 210 degrees centigrade and 3.1 MPa, and circulated to the second flash tank to flash. The third liquid discharged from the third evaporator can be subjected to heat exchange with the supplemented ammonia to obtain a sodium taurine solution. The flow rate of the sodium taurine was 279 Kg per hour, and the supplemented ammonia was added at a flow rate of 8.0 Kg per hour.

Contents of each component in the in the sodium taurine solution was tested. The content of sodium taurine was 14.3%, the content of sodium ditaurine was 0.65%, and the content of sodium tritaurine was 0.03%. The yield of the sodium taurine can be calculated, and was 98.43%.

In embodiment 7, unit consumption of the sodium taurine was 0.80 tons standard coal for 1 ton sodium taurine.

Embodiment 8

Sulfur dioxide was conveyed to 73.0 Kg of sodium hydroxide aqueous solution (which had a concentration of 18% by mass) until the pH reached 4.5, and 13.5 Kg ethylene oxide was added into the reaction system. The temperature of the reaction was controlled between 30 degrees centigrade and 40 degrees centigrade. The reaction ended when the pH was 11.0, and a sodium hydroxyethyl sulfonate-containing reaction liquid was obtained. A pH of a mother crystallization liquor was adjusted with an alkaline chamber liquid to 11.0. The sodium hydroxyethyl sulfonate-containing reaction liquid and the crystallization mother liquor were mixed in a storage tank, pressurized, mixed with circulating ammonia and conveyed to an aminolysis reaction system to reaction. The molar ratio of the ammonia to the sodium hydroxyethyl sulfonate was controlled to be 25:1, and a sodium taurine solution was obtained. The sodium taurine solution was filtered, diluted to a concentration of 10%, and subjected to acidification in a bipolar membrane electrodialysis system. An alkaline liquid having a concentration of 6% by mass was obtained in the alkaline chamber, and a taurine solution was obtained in the product chamber. The taurine solution was further compressed to a concentration 45%, crystallized to obtain the taurine product. A concentration of the taurine product was 99.4% by mass, and a total yield of the taurine product was 94% (including a yield of the mother liquor circulation).

Embodiment 9

Sulfur dioxide was conveyed to 73.0 Kg of sodium hydroxide aqueous solution (which had a concentration of 18% by mass) until the pH reached to 4.5, and 13.5 Kg ethylene oxide was added into the reaction system. The temperature of the reaction was controlled between 30 degrees centigrade and 40 degrees centigrade. The reaction ended when the pH was 11.0, and a sodium hydroxyethyl sulfonate-containing reaction liquid was obtained. A pH of a mother crystallization liquor was adjusted with an alkaline chamber liquid to 11.0. The sodium hydroxyethyl sulfonate-containing reaction liquid and the crystallization mother liquor were mixed in a storage tank, pressurized, mixed with circulating ammonia and conveyed to an aminolysis reaction system to reaction. The molar ratio of the ammonia to the sodium hydroxyethyl sulfonate was controlled to be 30:1, and a sodium taurine solution was obtained. The sodium taurine solution was filtered, diluted to a concentration of 10%, and subjected to acidification in a bipolar membrane electrodialysis system. An alkaline liquid having a concentration of 6% by mass was obtained in the alkaline chamber, and a taurine solution was obtained in the product chamber. The taurine solution was further compressed to a concentration 45%, crystallized to obtain the taurine product. A concentration of the taurine product was 99.6% by mass, and a total yield of the taurine product was 94.5% (including a yield of the mother liquor circulation).

Embodiment 10

Sulfur dioxide was conveyed to 73.0 Kg of sodium hydroxide aqueous solution (which had a concentration of 18% by mass) until the pH reached 4.5, and 13.5 Kg ethylene oxide was added into the reaction system. The temperature of the reaction was controlled between 30 degrees centigrade and 40 degrees centigrade. The reaction ended when the pH was 11.0, and a sodium hydroxyethyl sulfonate-containing reaction liquid was obtained. A pH of a mother crystallization liquor was adjusted with an alkaline chamber liquid to 11.0. The sodium hydroxyethyl sulfonate-containing reaction liquid and the crystallization mother liquor were mixed in a storage tank, pressurized, mixed with circulating ammonia and conveyed to an aminolysis reaction system to reaction. The molar ratio of the ammonia to the sodium hydroxyethyl sulfonate was controlled to be 35:1, and a sodium taurine solution was obtained. The sodium taurine solution was filtered, diluted to a concentration of 10%, and subjected to acidification in a bipolar membrane electrodialysis system. An alkaline liquid having a concentration of 6% by mass was obtained in the alkaline chamber, and a taurine solution was obtained in the product chamber. The taurine solution was further compressed to a concentration 45%, crystallized to obtain the taurine product. A concentration of the taurine product was 99.5% by mass, and a total yield of the taurine product was 95% (including a yield of the mother liquor circulation).

Embodiment 11

Sulfur dioxide was conveyed to 73.0 Kg of sodium hydroxide aqueous solution (which had a concentration of 18% by mass) until the pH reached 4.5, and 13.5 Kg ethylene oxide was added into the reaction system. The temperature of the reaction was controlled between 30 degrees centigrade and 40 degrees centigrade. The reaction ended when the pH was 11.0, and a sodium hydroxyethyl sulfonate-containing reaction liquid was obtained. A pH of a mother crystallization liquor was adjusted with an alkaline chamber liquid to 11.0. The sodium hydroxyethyl sulfonate-containing reaction liquid and the crystallization mother liquor were mixed in a storage tank, pressurized, mixed with circulating ammonia and conveyed to an aminolysis reaction system to reaction. The molar ratio of the ammonia to the sodium hydroxyethyl sulfonate was controlled to be 40:1, and a sodium taurine solution was obtained. The sodium taurine solution was filtered, diluted to a concentration of 10%, and subjected to acidification in a bipolar membrane electrodialysis system. An alkaline liquid having a concentration of 6% by mass was obtained in the alkaline chamber, and a taurine solution was obtained in the product chamber. The taurine solution was further compressed to a concentration 45%, crystallized to obtain the taurine product. A concentration of the taurine product was 99.6% by mass, and a total yield of the taurine product was 96.2% (including a yield of the mother liquor circulation).

Comparative Embodiment 1

The same operating method in embodiment 1 was used in comparative embodiment 1, and the molar ratio of the ammonia to the sodium hydroxyethyl sulfonate in the control system was 8:1.

The technological conditions of comparative embodiment 1 were shown hereinafter.

49.0 Kg ammonium hydroxide (which had a concentration of 25% by mass) and 36 Kg liquid ammonia were added into 170 Kg sodium hydroxyethyl sulfonate aqueous solution (which had a concentration of about 25% by mass) to obtain a mixture, wherein a molar ratio of the ammonia to the sodium hydroxyethyl sulfonate was 8:1. The mixture was pressurized to 18 MPa, then preheated to 280 degrees centigrade with a pre-heater, and conveyed to an aminolysis reactor to react. Temperature of the aminolysis reaction was 280 degrees centigrade, and the pressure of the aminolysis reaction was 18 MPa. After reacting for 30 minutes, the ammonia was removed from the aminolysis liquid to obtain 205.5 Kg sodium taurine solution, wherein the content of sodium taurine was 8% by mass and the yield of the sodium taurine was 64.85%.

Comparative Embodiment 2

The same operating method in embodiment 1 was used in comparative embodiment 2, and the molar ratio of the ammonia to the sodium hydroxyethyl sulfonate in the control system was 120:1.

The technological conditions of comparative embodiment 2 were shown hereinafter.

400.0 Kg ammonium hydroxide (which had a concentration of 25% by mass) and 623.7 Kg liquid ammonia were added into 170 Kg sodium hydroxyethyl sulfonate aqueous solution (which had a concentration of about 25% by mass) to obtain a mixture, wherein a molar ratio of the ammonia to the sodium hydroxyethyl sulfonate was 120:1. The mixture was pressurized to 18 MPa, then preheated to 280 degrees centigrade with a pre-heater, and conveyed to an aminolysis reactor to react. Temperature of the aminolysis reaction was 280 degrees centigrade, and the pressure of the aminolysis reaction was 18 MPa. After reacting for 30 minutes, the ammonia was removed from the aminolysis liquid to obtain 465 Kg sodium taurine solution, wherein the content of sodium taurine was 5.38% by mass and the yield of the sodium taurine was 98.7%.

Comparative Embodiment 3

In comparative embodiment 3, aminolysis reaction of the sodium hydroxyethyl sulfonate and the ammonia and post-processing of the ammonia were carried out by a conventional method.

A sodium hydroxyethyl sulfonate aqueous solution (which had a concentration of 15% by mass) was mixed with a mixture of the liquid ammonia and the ammonium hydroxide. A flow rate of the sodium hydroxyethyl sulfonate aqueous solution was 272 Kg per hour. A molar ratio of the ammonia to the sodium hydroxyethyl sulfonate was controlled to be 30:1. The mixture was pressurized to 18 MPa via a high-pressure pump, and preheated to 280 degrees centigrade. The resultant mixture was conveyed to an aminolysis reactor and reacted in conditions at 18 MPa and 280 degrees centigrade. The reaction lasted for 30 minutes, and an aminolysis reaction liquid was obtained. The aminolysis liquid was conveyed to the evaporator to obtain a sodium taurine solution (which has a concentration of 13.8%). The flow rate of the sodium taurine solution was 278 Kg per hour. The operating pressure of the evaporator was 0.1 MPa, and the operating temperature of the evaporator was 97 degrees centigrade. An ammonia-containing resultant obtained by evaporation was condensed by a condenser, and conveyed to an ammonia still to recycle. Supplemented ammonia was added into the recycled ammonia, and circulated to the aminolysis reactor to react again.

Contents of each component in the in the sodium taurine solution was tested. The content of sodium taurine was 13.7%, the content of sodium ditaurine was 1.1%, and the content of sodium tritaurine was 0.1%. The yield of the sodium taurine can be calculated, and was 93.9%.

In comparative embodiment 3, unit consumption of the sodium taurine was 3.72 tons standard coal for 1 ton sodium taurine.

Comparative Embodiment 4

In comparative embodiment 4, aminolysis reaction of the sodium hydroxyethyl sulfonate and the ammonia and post-processing of the ammonia were carried out by conventional method.

A sodium hydroxyethyl sulfonate aqueous solution (which had a concentration of 15% by mass) was mixed with a mixture of the liquid ammonia and the ammonium hydroxide. A flow rate of the sodium hydroxyethyl sulfonate aqueous solution was 272 Kg per hour. A molar ratio of the ammonia to the sodium hydroxyethyl sulfonate was controlled to be 30:1. The mixture was pressurized to 18 MPa via a high-pressure pump, and preheated to 280 degrees centigrade. The resultant mixture was conveyed to an aminolysis reactor and reacted in conditions at 18 MPa and 280 degrees centigrade. The reaction lasted for 30 minutes, and an aminolysis reaction liquid was obtained. The aminolysis reaction liquid was conveyed to a first flash tank, a second flash tank and a third evaporator, respectively; and a sodium taurine solution was obtained. The flow rate of the sodium taurine solution was 278 Kg per hour. The operating pressure of the first flash tank was 8 MPa, and the operating temperature of the first flash tank was 241 degrees centigrade. The operating pressure of the second flash tank was 3 MPa, and the operating temperature of the second flash tank was 203 degrees centigrade. The operating pressure of the third evaporator was 0.1 MPa, and the operating temperature of the third evaporator was 97 degrees centigrade. Ammonia-containing resultants obtained by flashing and evaporation were condensed by condensers, respectively, and conveyed to an ammonia still to recycle. Supplemented ammonia was added into the recycled ammonia, and circulated to the aminolysis reactor to react again.

Contents of each component in the in the sodium taurine solution was tested. The content of sodium taurine was 13.8%%, the content of sodium ditaurine was 1.2%, and the content of sodium tritaurine was 0.1%. The yield of the sodium taurine can be calculated, and was 94.59%.

In comparative embodiment 3, unit consumption of the sodium taurine was 1.32 tons standard coal for 1 ton sodium taurine.

In the aminolysis reaction of the comparative embodiment 1, the molar ratio of the ammonia to the sodium hydroxyethyl sulfonate was low. The yield of the comparative embodiment 1 was only 64.85%, and the content of the sodium ditaurine and the sodium tritaurine in the aminolysis product was relatively high. In comparative embodiment 2, the molar ratio of the ammonia to the sodium hydroxyethyl sulfonate was greater than 100. The yield of the comparative embodiment 2 was as high as 98.7%, but the cost for recycling the ammonia was relatively high, and the yield increase was little compared with that of embodiment 8. In comparative embodiment 3 and comparative embodiment 4, the compression units were different from those of the present disclosure. In addition, the recycled ammonia was not transformed to a supercritical fluid to circulate, but an ammonia-containing gas obtained by the ammonia separator was directly treated in an ammonia still and the recycled high ammonia-containing resultant was circulated and subjected to the aminolysis step. Compared with embodiment 3 and embodiment 5, it can be concluded that when the same ammonia separator was used, the energy consumption of the ammonia recycly method in the comparative embodiment 3 and 4 was much greater than that of the aminolysis reaction system in the present embodiment, and this increased the cost of production.

The technical features of the above-described embodiments may be combined in any combination. For the sake of brevity of description, all possible combinations of the technical features in the above embodiments are not described. However, as long as there is no contradiction between the combinations of these technical features, all should be considered as within the scope of this disclosure.

The above-described embodiments are merely illustrative of several embodiments of the present disclosure, and the description thereof is relatively specific and detailed, but is not to be construed as limiting the scope of the disclosure. It should be noted that a number of variations and modifications may be made by those skilled in the art without departing from the spirit and scope of the disclosure. Therefore, the scope of the disclosure should be determined by the appended claims.

We claim:

1. A method for preparing sodium taurine as a taurine intermediate, comprising:
   providing sodium hydroxyethyl sulfonate and an ammonia source; and
   feeding the sodium hydroxyethyl sulfonate and the ammonia source into an aminolysis reactor for an aminolysis reaction to obtain a mixture containing sodium taurine as a taurine intermediate, wherein a molar ratio of ammonia in the ammonia source to the sodium hydroxyethyl sulfonate is greater than or equal to 25:1, and
   after the aminolysis reaction, separating unreacted ammonia from the mixture with an ammonia separating device, so as to obtain an ammonia-containing gas and the taurine intermediate, respectively, wherein the ammonia separating device is connected to the aminolysis reactor; and
   compressing the ammonia-containing gas with a compression unit to obtain a supercritical fluid containing ammonia, and circulating the supercritical fluid to the aminolysis reactor, wherein the compression unit is connected to the ammonia separating device and the aminolysis reactor, respectively.

2. The method of claim 1, wherein the ammonia separating device comprises one ammonia separator.

3. The method of claim 1, wherein the ammonia separating device comprises two ammonia separators, which are defined as a first ammonia separator and a second ammonia separator, respectively;
   wherein the first ammonia separator is connected to the aminolysis reactor, the first ammonia separator is configured for separating the unreacted ammonia from the mixture after the aminolysis reaction to obtain a first ammonia-containing gas and a first residuum mixture; and
   wherein the second ammonia separator is connected to the first ammonia separator, the second ammonia separator is configured for further separating ammonia gas from the first residuum mixture to obtain a second ammonia-containing gas and a second residuum, and circulating the second ammonia-containing gas to the first ammonia separator.

4. The method of claim 3, wherein the compression unit comprises a first compression unit and a second compression unit;
   wherein the first compression unit is connected to the first ammonia separator and the aminolysis reactor, respectively, and the first compression unit is configured for compressing the ammonia-containing gas in the first ammonia separator to obtain the supercritical fluid, and circulating the supercritical fluid to the aminolysis reactor; and
   wherein the second compression unit is connected to the first ammonia separator and the second ammonia separator, respectively, and the second compression unit is configured for circulating the second ammonia-containing gas to the first ammonia separator.

5. The method of claim 1, wherein the ammonia separating device comprises a plurality of sequentially arranged ammonia separators, a number of the plurality of ammonia separators is n, and n is an integer which is greater than 2 and less than 20;
   wherein a first ammonia separator of the plurality of ammonia separators is connected to the aminolysis reactor, the first ammonia separator is configured for separating the unreacted ammonia from the mixture after the aminolysis reaction to obtain a first ammonia-containing gas and a first residuum mixture;
   wherein a second ammonia separator of the plurality of ammonia separators is connected to the second ammonia separator, the second ammonia separator is configured for further separating ammonia gas from the first residuum mixture to obtain a second ammonia-containing gas and a second residuum, and circulating the second ammonia-containing gas to the first ammonia separator; and
   wherein an $i^{th}$ ammonia separator of the plurality of ammonia separators is connected to an $i\text{-}1^{th}$ ammonia separator, wherein i is an integer which is greater than 2 and less than or equal to an integer 'n', the $i^{th}$ ammonia separator is configured for further separating ammonia gas from an $i\text{-}1^{th}$ residuum mixture to obtain an $i^{th}$ ammonia-containing gas and an $i^{th}$ residuum, and circulating the $i^{th}$ ammonia-containing gas to the $i\text{-}1^{th}$ ammonia separator.

6. The method of claim 5, wherein the aminolysis reaction is conducted through an aminolysis reaction system comprising a plurality of compression units, a number of the plurality of compression units is n;
   wherein a first compression unit of the plurality of compression units is connected to the first ammonia separator and the aminolysis reactor, respectively, and the first compression unit is configured for compressing the ammonia-containing gas in the first ammonia separator to obtain the supercritical fluid, and circulating the supercritical fluid to the aminolysis reactor;
   wherein a second compression unit of the plurality of compression units is connected to the first ammonia separator and the second ammonia separator, respectively, and the second compression unit is configured for circulating the second ammonia-containing gas to the first ammonia separator; and
   wherein an $i^{th}$ compression unit of the plurality of compression units is connected to the $i\text{-}1^{th}$ ammonia separator and the $i^{th}$ ammonia separator, respectively, and the $i^{th}$ compression unit is configured for circulating the $i^{th}$ ammonia-containing gas to the $i\text{-}1^{th}$ ammonia separator.

7. The method of claim 5, wherein n is equal to three or four.

8. The method of claim 1, further comprising a step of supplementing the ammonia source into the ammonia separating device.

* * * * *